(12) United States Patent
Lareau et al.

(10) Patent No.: US 8,876,797 B2
(45) Date of Patent: *Nov. 4, 2014

(54) CATHETERS WITH HIGH-PURITY FLUOROPOLYMER ADDITIVES

(71) Applicant: AngioDynamics, Inc., Latham, NY (US)

(72) Inventors: Raymond Lareau, Westford, MA (US); Benjamin Bell, Shrewsbury, MA (US); J. Paul Santerre, Whitby (CA); Jeannette Ho, Toronto (CA)

(73) Assignee: AngioDynamics, Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/100,671

(22) Filed: Dec. 9, 2013

(65) Prior Publication Data

US 2014/0276641 A1    Sep. 18, 2014

Related U.S. Application Data

(63) Continuation of application No. 13/950,592, filed on Jul. 25, 2013, now Pat. No. 8,603,070.

(60) Provisional application No. 61/790,821, filed on Mar. 15, 2013.

(51) Int. Cl.
*A61M 25/098* (2006.01)
*A61L 29/18* (2006.01)
*A61L 29/04* (2006.01)
*A61L 33/06* (2006.01)

(52) U.S. Cl.
CPC .............. *A61L 29/049* (2013.01); *A61L 29/18* (2013.01); *A61L 33/062* (2013.01)
USPC .......................... 604/529; 604/520; 524/423

(58) Field of Classification Search
USPC .................................... 604/523, 529; 524/423
See application file for complete search history.

(56) References Cited

U.S. PATENT DOCUMENTS

| | | |
|---|---|---|
| 6,127,507 A | 10/2000 | Santerre |
| 8,187,234 B2 | 5/2012 | Weaver et al. |
| 8,267,915 B2 | 9/2012 | Daly et al. |
| 8,377,011 B2 | 2/2013 | Weaver et al. |
| 2005/0171490 A1 | 8/2005 | Weaver et al. |
| 2005/0171510 A1 | 8/2005 | Dicarlo et al. |

*Primary Examiner* — Peter Szekely
(74) *Attorney, Agent, or Firm* — Kacvinsky Daisak Bluni PLLC

(57) ABSTRACT

The present invention provides catheter compositions that provide anti-thrombogenic properties while not adversely impacting mechanical properties. All embodiments of the present invention comprise a catheter that comprises a fluoropolymer additive with specific compositions and/or purity levels.

10 Claims, 1 Drawing Sheet

CATHETERS WITH HIGH-PURITY FLUOROPOLYMER ADDITIVES

RELATED APPLICATION

This application is a continuation of U.S. patent application Ser. No. 13/950,592 filed Jul. 25, 2013, (issued as U.S. Pat. No. 8,603,070 on Dec. 10, 2013) which in turn claims priority to and the benefit of U.S. Provisional Patent Application Ser. No. 61/790,821, filed on Mar. 15, 2013, the disclosure of which is hereby incorporated by reference in its entirety.

FIELD OF THE INVENTION

The present invention relates to catheters, and more specifically to indwelling catheters that comprise fluoropolymer additives.

BACKGROUND

There are numerous examples of catheters and other implantable medical devices that are placed into a patient's vasculature for prolonged periods of time, such as central venous catheters ("CVCs"), implantable ports ("Ports"), dialysis catheters and peripherally-inserted central catheters ("PICCs"). These devices may be used to deliver therapeutic agents and other fluids to patients over numerous weeks.

Inherent with the use of medical devices that are placed into a patient's vasculature or other blood-containing environments is the aggregation of platelets on the device surface, thus leading to a risk of thrombus formation, which can, in turn, result in catheter complications including both catheter related blood stream infection and thrombosis. Thrombus formation on catheter surfaces has been the subject of much research and product development efforts. For example, attempts to minimize thrombus formation on catheter surfaces have the incorporation of heparin, albumin and endothelial cells on the catheter surfaces. The permanent binding of biologically active moieties to catheter polymer chains or polymer surfaces has also been studied.

In U.S. Pat. No. 6,127,507, which is incorporated herein by reference for all purposes, it is proposed to use certain fluoroalkyl surface-modifying macromolecules in admixture with elastomers for the manufacture of blood-contacting medical devices. It is believed that the use of such macromolecules can result in a reduction in thrombosis formation on the medical device surfaces.

While additives such as fluoropolymers and other materials may impart beneficial properties to implantable medical devices, their addition to polymeric materials used to manufacture the medical devices may also adversely impact mechanical properties. The purity of such additives may also adversely impact these properties. As such, there is a need for additive compositional and/or purity requirements that yield advantageous anti-thrombogenic properties without compromising desired mechanical properties of medical devices made from materials that incorporate such additives.

SUMMARY

In one aspect, the present invention provides catheter compositions that provide anti-thrombogenic properties while not adversely impacting mechanical properties.

In another aspect, the present invention provides methods of treating patients using catheters made from compositions that provide anti-thrombogenic properties while not adversely impacting mechanical properties.

In yet another aspect, the present invention provides kits that comprise catheters made from compositions that provide anti-thrombogenic properties while not adversely impacting mechanical properties.

In yet another aspect, the present invention provides methods of instructing healthcare providers to treat patients using catheters made from compositions that provide anti-thrombogenic properties while not adversely impacting mechanical properties.

All embodiments of the present invention comprise a catheter that comprises a fluoropolymer additive. The catheter that comprises an elongated tubular structure comprising a polymeric material, an outer surface, a proximal end, a distal end, and a lumen. The outer surface and the lumen extend between the device proximal and distal ends.

In certain embodiments, the catheter is characterized by a wall thickness between said outer surface and said lumen of 0.005 to 0.050 inches. In such embodiments, the catheter comprises a polymeric material comprising polyurethane and additives, which comprise a radiopaque material and a fluoropolymer comprising terminal polyfluoro-oligomeric groups. The additives comprise up to about 44 weight percent of said polymeric material.

In other embodiments, the catheter comprises a polymeric material comprising a fluoropolymer comprising terminal polyfluoro-oligomeric groups, wherein the fluoropolymer is characterized by a polystyrene equivalent weight average molecular weight ($M_w$) greater than 13,000 Daltons (13 kDa).

DESCRIPTION OF PREFERRED EMBODIMENTS

The present invention provides for catheters that have compositions that provide superior anti-thrombogenic properties while not adversely impacting mechanical properties such as strength and toughness. As used herein, "catheter" means any polymeric medical conduit that can be inserted into a patient's body to treat diseases, administer or withdraw fluids, or to perform a surgical procedure. The catheters of the present invention are applicable to placement within the vascular, urological, gastrointestinal, ophthalmic, and other bodily systems, and may be inserted into any suitable bodily lumen, cavity or duct. The catheters of the present invention may comprise one, two, three, or four lumens, and preferably include indwelling catheters, which are catheters left inside the patient's body in either a temporary or permanent basis. Such catheters include, for example, CVCs, PICCs, ports, hemodialysis catheters, renal infusion systems, and drainage catheters.

Figure 1:
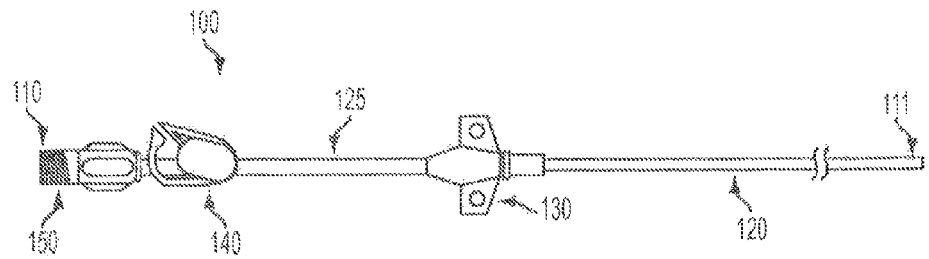
FIG. 1 is a perspective view of a single-lumen PICC catheter, in accordance with an embodiment of the present invention.
Figure 2:
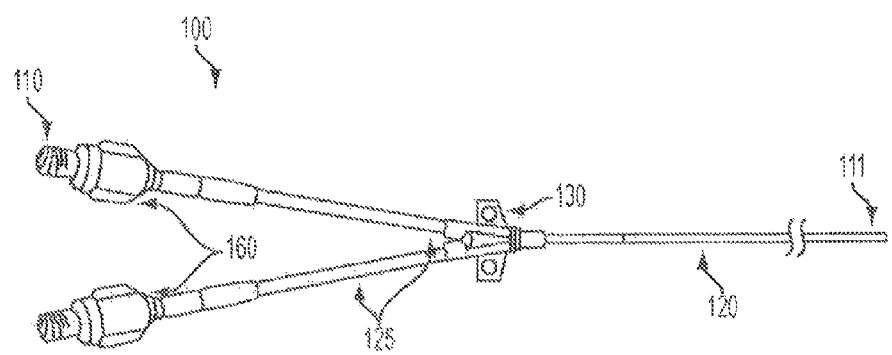
FIG. 2 is a perspective view of a dual-lumen PICC catheter, in accordance with an embodiment of the present invention.
Figure 3:
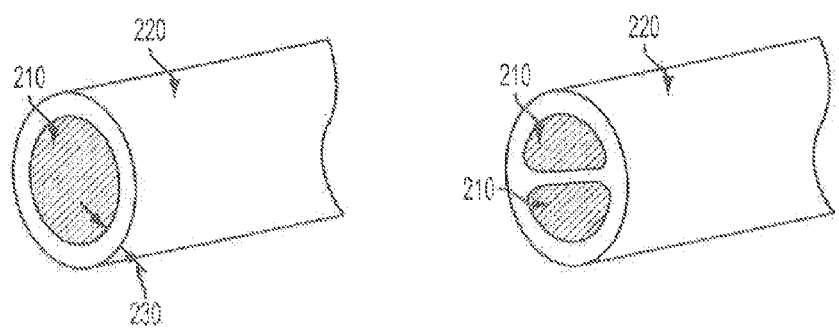
FIG. 3 shows cross-sectional views of single- and dual-lumen catheter devices, in accordance with embodiments of the present invention.

The present invention is described with particular reference to a PICC catheter, such as the BioFlo PICC (marketed by Angiodynamics, Inc., Latham, N.Y.). It should be appreciated, however, that the invention is equally applicable to catheters of any type or configuration. FIG. 1 illustrates an example of a PICC as an embodiment of the present invention. The PICC 100 comprises a proximal end 110 and a distal end 111. The PICC 100 may be characterized in the industry as having a catheter portion 120 (which is inserted into a patient) and an extension tube 125 (which remains outside of the patient's body), separated by a suture wing 130 (which may be attached via suture or other suitable means to the patient's skin). For purposes of the present invention, however, the term "catheter" shall apply either of the entirety of PICC 100 or just the portion 120, as may be applicable. PICC 100 further comprises a clamp 140 and luer lock hub 150, as are known in the art. The PICC 100 shown in FIG. 1 is a single-lumen catheter, meaning that only one lumen extends between proximal and distal ends 110, 111. In other embodiments, the PICC 100 includes multiple lumens. For example, PICC 100 shown in FIG. 2 includes two lumens that separate proximal to the suture wing 125. In cross-section, the catheter portion 120 of the embodiments shown in FIGS. 1 and 2 can be seen in FIG. 3, which show the single lumen (left) and dual-lumen (right) embodiments comprising inner lumen(s) 210, outer surface 220, and a wall thickness 230 between the lumen(s) 210 and the outer surface 220. Triple- and quadruple-lumen PICCs and other catheters may also be used in the present invention. Another non-limiting difference between the embodiments shown in FIGS. 1 and 2 is that the PICC 100 shown in FIG. 2 makes use of in-line slit valves 160 (marketed as PASV valves by Angiodynamics, Inc., Latham, N.Y.) rather than clamps 140. Examples of such slit valves are described in U.S. Pat. No. 8,377,011 entitled "Pressure Activated Valve with High Flow Slit," filed on Aug. 31, 2011 naming Karla Weaver and Paul DiCarlo as inventors; U.S. application Ser. No. 10/768,571 entitled "Pressure Activated Safety Valve With Anti-Adherent Coating" filed on Jan. 29, 2004 naming Karla Weaver and Paul DiCarlo as inventors, U.S. application Ser. No. 10/768,629 entitled "Stacked Membrane For Pressure Actuated Valve" filed on Jan. 29, 2004 naming Karla Weaver and Paulo DiCarlo as inventors, and U.S. application Ser. No. 10/768,855 entitled "Pressure Actuated Safety Valve With Spiral Flow Membrane" filed on Jan. 29, 2004 naming Paul DiCarlo and Karla Weaver as inventors, and U.S. application Ser. No. 10/768,479 entitled "Dual Well Port Device" filed on Jan. 29, 2004 naming Katie Daly, Kristian DiMatteo and Eric Houde as inventors. Each of the aforementioned patents and patent applications are incorporated herein by reference in their entireties for all purposes.

The size of the catheter used in the present invention will depend upon the applicable clinical application. For example, PICCs are typically manufactured to have an outer diameter from 1.5-7 French (with 1.5 French corresponding to 0.5 mm/0.019 in; 3 French corresponding to 1 mm/0.039 in; 4 French corresponding to 1.33 mm/0.053 in, 5 French corresponding to 1.67 mm/0.066 in, 6 French corresponding to 2 mm/0.079 in; and 7 French corresponding to 2.3 mm/0.091 in). In certain embodiments, single-lumen catheters are manufactured to 3, 4, and 5 French; dual-lumen catheters are manufactured to 5 and 6 French, and triple-lumen catheters are manufactured to 6 French. Example wall thicknesses for single-lumen embodiments are within the range of 0.004 to 0.060 inches, preferably 0.0075 to 0.0110 inches. Example wall thicknesses for dual-lumen embodiments are within the range of 0.0040 to 0.060 inches, preferably 0.0075 to 0.0110 inches. Example wall thicknesses for triple-lumen embodiments are within the range of 0.004 to 0.060 inches, preferably about 0.0075 to 0.0110 inches. All sizes expressed herein are intended to be nominal average sizes, rather than a strict specification of a constant catheter dimension at all locations.

The PICC catheters shown in FIGS. 1 and 2 are indicated for short or long-term peripheral access to the central venous system for intravenous therapy, including but not limited to, the administration of fluids, medications, and nutrients; the sampling of blood; for central venous pressure monitoring and for power injection of contrast media during surgical procedures. In a preferred embodiment, the catheters of the present invention are "power injectable" in the sense that they are able to withstand the high pressures associated with the injection of fluid contrast media during cardiac procedures, as known in the art. Because such catheters are inserted into a patient's vasculature an exposed to blood and other bodily fluids for some period of time, precautions are made to minimize the risk of catheter related blood stream infection and thrombus formation. The catheter materials of the present invention provide this desired effect without degrading mechanical properties of the catheter.

The catheters of the present invention provide a unique and beneficial combination of anti-thrombogenic and mechanical properties. As used herein, the catheters of the present invention are said to be "anti-thrombogenic" or "thromboresistant" (which terms are used interchangeably in this specification) because they are more resistant to the accumulation of blood components than conventional catheter materials. While not wishing to be bound by theory, the inventors believe that the polymer compositions of the present invention provide a catheter surface and bulk that is unsuitable to the attachment or accumulation of blood components. As such, the catheters of the present invention achieve anti-thrombogenic properties not by drug delivery or by any therapeutically active means, but rather by providing a catheter surface and bulk to which blood components do not easily attach. Moreover, it should be understood that "anti-thrombogenic," as used herein, should not be limited to the complete elimination of thrombus buildup related to the catheter.

The catheters of the present invention preferably comprise polyurethane. One example of a suitable polyurethane material that is known in the art is CARBOTHANE® (Lubrizol Advanced Materials, Inc., Cleveland, Ohio), which is a family of aliphatic, polycarbonate-based thermoplastic polyurethanes. Although polyurethanes are used as the preferred primary component in the materials used to make the catheters of the present invention, it is contemplated that other polymeric materials such as silicone may also be used.

The catheters of the present invention are manufactured from polymeric materials that comprise additives that are incorporated into the polymeric material. As used herein, "additives" refer to any materials that are added into the polymeric materials of the present invention to influence physical, mechanical, or other material properties, or to advantageously impact manufacturability or desired performance characteristics. Examples of known additives for polymeric materials include pigments (used synonymously herein with colorants), biostabilizers, plasticizers, nucleating agents fillers, radiopaque powders (or other forms), and materials in any form that enhance biocompatibility or other in vivo performance characteristics.

An example of a fluoropolymer additive that is used in embodiments of the present invention is marketed under the trade name ENDEXO™ (Interface Biologics Inc., Toronto, Ontario Canada), which generally refers to a fluoropolymer additive material described in U.S. Pat. No. 6,127,507, which is incorporated herein for all purposes. As used herein, "fluoropolymer" means a fluorocarbon-based polymer, including oligomers, having carbon-fluorine bonds. In a preferred embodiment, the fluoropolymer used in the present invention is a fluoroalkyl fluoropolymer that is characterized by terminal polyfluoro oligomeric groups.

The additives used in the catheter compositions of the present invention may be distributed throughout the entirety of the catheter, or preferably in one or more sections of the catheter that come into contact with blood or other bodily fluids. For example, in the embodiment shown in FIG. 1, catheter portion 120 may contain the additives but extension tube 125 optionally does not contain the additives. Moreover, the additives may be homogeneously distributed throughout the catheters of the present invention, or may be distributed such that the additive concentration varies along the catheter length or within the catheter wall thickness (i.e., stratified between the catheter outer wall and an inner lumen).

The preferred embodiment of a fluoropolymer additive is now described in detail. As described in U.S. Pat. No. 6,127,507, this additive may be referred to as a "surface modifying molecule" or "SMM." The surface modifying macromolecule has a central portion and terminal groups, the central portion being a member selected from the group consisting of a soft central portion and a hard central portion, the central portion having a molecular weight of less than 5,000 and including a segmented oligomeric copolymer unit including at least one polar segment and at least one hydrophobic segment, and the terminal groups including α-ω terminal polyfluoro oligomeric groups. Preferably the oligomeric copolymer unit has a molecular weight of less than 5000, e.g. less than 2000 such as 200-1200. By the term "segmented" is meant a relatively short length of a repeating unit, generally less than about 10 monomeric units having, preferably, structural formulas such as ABAB, wherein A represents a polar hard segment chemically bonded to a soft block B. Preferably, the polyfluoro oligomeric group is a perfluoroalkyl group; and the polar hard segment is selected from the group consisting of a urethane, ester, amide, sulfonamide and carbonate. In a preferred aspect the invention provides a composition comprising in admixture a polyurethane elastomer and a compatible surface-modifying macromolecule in a surface-modifying enhancing amount, wherein said polyurethane elastomer has a molecular weight of at least 2 times the molecular weight of said SMM.

The SMM additives, when used in embodiments of the invention, are preferably synthesized in a manner that they contain a base polymer compatible segment and terminal hydrophobic fluorine components which are non-compatible with the base polymer. The compatible segment of the SMM is selected to provide an anchor for the SMM within the base polymer substrate upon admixture. While not being bound by theory, it is believed that the fluorine tails are responsible in part for carrying the SMM to the surface of the admixture, with the chemical resistant fluorine chains exposed out from the surface. The latter process is believed to be driven by the thermodynamic incompatibility of the fluorine tail with the polymer base substrate, as well as the tendency towards establishing a low surface energy at the mixture's surface. When the balance between anchoring and surface migration is achieved, the SMM remains stable at the surface of the polymer, while simultaneously altering surface properties. The utility of the additives of the invention versus other known macromolecular additives, lies in 1) the molecular arrangement of the amphipathic segments in the SMM chain, i.e. two-ω fluoro-tails, one at each end, with the polar segment sandwiched between them; 2) the molecular weight of the fluorine tails relative to that of the central segment and; 3) the ability of the materials to inhibit biodegradation of the base polymer when the fluoro-segments are stabilized at the interface, which provides improved blood compatibility and biostability of the base polymers. This latter improvement has not been previously achieved and/or demonstrated with any other family of amphipathic polymeric type surface modifying macromolecules.

The surface modifying macromolecules used in embodiments of the present invention significantly alter the surface chemistry of, for example, segmented polyurethanes, i.e. the SMMs migrate to the surface of the polymer mixture and exhibit a new hydrophobic domain. This new surface carries many of the attributes of the perfluoro-carbon chains and, therefore, can have improved hemocompatibility.

The SMM additives used in embodiments of the present invention are, for example, of use with linear or crosslinked polyurethane-based materials. By tailoring the central segment components of the SMM, the fluoropolymer additives can be applied inter alia to a wide range of polymer materials which include polymers synthesized with reagents that are of common knowledge in the field of polyurethanes.

There are no restrictions on the specific stoichiometry of the reagents used in the synthesis of the SMM fluoropolymers used in embodiments the present invention, the manner in which they are added to each other, the temperature, pressure or atmosphere under which they are synthesized or the use of catalysts in their reaction. However, the molecular weight of the soft segments (i.e., those parts of the central segment components that are not polar hard segments) are, typically, between 200 and 5000. It is not desirable to simultaneously synthesize a SMM additive with the base polymer to which they are admixed, since the synthesis of the SMM additive is sensitive to reaction conditions. However, the SMM additives may be added to the synthesized base polymer, immediately following the latter's synthesis, in such a manner as to incorporate the SMM additives into the base polymer substrate prior to the final work-up of the polymer substrate.

Embodiments of SMM fluoropolymer additives used in the present invention may be synthesized using a multi-functional isocyanate, a multi-functional soft segment precursor reactive therewith, and a mono function polyfluoro-alcohol. The isocyanate is preferably, but not so limited to be di-functional in nature, in order to favour the formation of a linear SMM. Linear as opposed to branched or crosslinked SMM have better migration properties within the polyurethane substrate. A preferred diisocyanate for biomedical applications is 1,6-hexanediisocyanate. The soft segment precursor molecule is preferably di-functional in nature but not so limited to be di-functional, in order to favour the formation of a linear SMM. Again, linearity favours migration properties within the base polymer substrate. Examples of typical soft segment precursors include, polypropylene oxide polyols of molecular weight 1000, and polytetramethylene oxide diols of molecular weight 1000. SMM's are synthesized using a preliminary prepolymer method similar to the classical one used for polyurethanes. However, the subsequent step differs in that a chain extension is not carried out. A monofunctional oligomeric fluorinated alcohol is used to cap the prepolymer, rather than chain extend the prepolymer. The fluorinated alcohol preferably has a single fluoro-tail but is not limited to this feature. A general formula for the oligomeric fluoro-alcohol of use in the invention is $H-(OCH_2CH_2)_n-(CF_2)_m-CF_3$, wherein n can range from 1 to 10, but preferably ranges from 1 to 4, and m can range from 1 to 20 but preferably ranges from 2 to 12. A general guide for the selection of "n" relative to "m" is that "m" should be equal or greater to "2n" in order to minimize the likelihood of the $(OCH_2CH_2)_n$ segment displacing the $(CF_2)_m-CF_3$ from the surface following exposure to water, since the former is more hydrophilic than the fluorotail and will compete with the fluorotail for the surface. Without being bound by theory, the presence of the $(OCH_2CH_2)_n$ segment is believed to be important to the function of the SMM because it provides a highly mobile spacer segment between the fluorotail and the substrate. This is important in order to effectively expose the fluorosurface to, for example, an aqueous medium. Examples of typical oligomeric fluoroalcohols include various fractions BA-L, BA-N, FSO-100 and FSN-100 (DuPont de Nemours, Wilmington, Del.).

Examples of SMM fluoropolymer additives used in the present invention can be synthesized with different components and stoichiometry. Prior to synthesis, the isocyanate is, preferably, vacuum distilled to remove residual moisture. Soft segment precursors are degassed overnight to remove residual moisture and low molecular weight organics. In an example where BA-L is used as the fluoroalcohol, this reagent is fractionated into three fractions to reduce the distribution of molecules with different "m" values. This reduces the selective reaction of a fluoro-alcohol of a particular "m" value over another. The BA-L fractions were characterized as (i) a first fraction, herein called BA-L (Low) which is a clear liquid distilled at 102.degree. C. and atmospheric pressure; (ii) a second fraction referred to as BA-L (Intermediate), which is a white semi-solid material, distilled between 70 and 80.degree. C. under a vacuum of 0.01 mm Hg pressure; and (iii) a last fraction referred to as BA-L (High) and is distilled between 80 and 100.degree. C. under a vacuum of 0.01 mm Hg as a very pale yellow solid. The selection of these fractions is somewhat arbitrary and it will be apparent to those skilled in the art that different fractions can be selected to alter the nature of the SMM in order to tailor the material for specific applications with base polymers. It is preferable to use organic solvents compatible with the chemical nature of the reagents in order to have good control over the characteristics of the final product. Typical organic solvents include dimethyl acetamide, acetone, tetrahydrofuran and dimethyl sulfoxide. A preferred reaction solvent is N, N-dimethylacetamide (DMAC, Aldrich Chemical Company, Milwaukee, Wis.). In view of the low reaction activity of some diisocyanates, e.g. HDI, with soft segment precursor diols, a catalyst is preferred for the synthesis. Typical catalysts are similar to those used in the synthesis of polyurethanes and, include, dibutyltin dilaurate, stannous octoate, N,N-diethylcyclohexylamine, N-methylmorpholine, tetramethylbutane-dianine and 1,4 diazo (2,2,2) bicyclooctane.

In the first step of the preparation of an exemplary SMM fluoropolymer additive used in embodiments of the present invention, the isocyanate is added to the soft segment component and, optionally, catalyst to provide a prepolymer. Subsequently the fluoro-alcohol is added to the prepolymer and generally the mixture allowed to react overnight. The SMM polymer is precipitated in distilled water, washed to remove any residual fluoro-alcohol and dried. The SMM can be manipulated and handled for use with base polymers in the same manner as the polymers per se can be handled in the fabrication of article products. The SMM may be admixed with, for example, polyurethane base polymer 1) by compounding methods for subsequent extrusion or injection molding of articles; 2) by co-dissolving the polyurethane and SMM into a solvent of common compatibility for subsequent casting of an article in a mold or for spinning fibers to fabricate an article; or 3) by wetting the surface of a polyurethane with a solution of SMM in a solvent of common compatibility with the polyurethane to which the SMM solution is being applied.

The SMM fluoropolymer additives used in embodiments of the present invention provide, in one aspect, a series of fluorine-containing oligomeric surface modifying macromolecules. When used in admixture with, for example, a polyurethane, the SMM's inhibit polyurethane degradation by enzyme action. The SMMs are copolymers or terpolymers that have the ability to alter the surface chemistry and, hence, surface properties of a polymer and are synthesized in such a manner that (i) preferably, they have a lower molecular weight than the base material i.e. the polymer that requires protection from biodegradation and (ii) they contain a surface active segment containing (α-ω terminal polyfluoro groups.

SMM fluoropolymer additives used in embodiments of the present invention thus contain, preferably as α-ω terminal groups, fluoropolymeric segments comprising a sequential group of carbon atoms containing fluorine atoms and constituting an oligomeric chain. Preferred perfluorinated alcohols of use in the practice of the invention are those of the general formula $CF_3 (CF_2)_n CH_2CH_2OH$, having a linear alkyl chain, wherein n is 5-9, most preferably $C_8F_{17}CH_2CH_2OH$. These monomers are commercially available under the trademark ZONYL (du Pont de Nemours, Wilmington, Del., USA) as homologous mixtures having varying degrees of fluoralkane chain lengths. One such preferred mixture available under the name BA-L has an average molecular weight of 443; fluorine content of 70%; S.G. 1.5@30.degree. C.; thickening point<25.degree. C. and a boiling range of 102-175.degree. C.@50 mm Hg.

The use of fluoropolymer additives, as described herein, is beneficial to achieving desired catheter anti-thrombogenic properties without the need for surface coatings. As such, the catheters of the present invention preferably do not contain heparin, thus minimizing the risk of complications associated with heparin use. The additives, including the fluoropolymer are preferably present throughout the catheter material, including the outer surface, inner surface and even the cut catheter tip.

In addition to fluoropolymer additives such as those described herein, other preferred additives used in the polyurethanes or other materials of the catheters of the present invention include radiopaque materials such as powders or other particulates. Suitable radiopaque additives include bismuth subcarbonate, bismuth oxychloride, bismuth trioxide, tungsten, and preferably barium sulfate. Other additives used in the present invention include colorants such as pigments, dyes, or other suitable materials.

The inventors have found that the amount and/or composition of additives used in the polymer compositions of the present invention are important for providing a unique and surprising combination of anti-thrombogenic properties and mechanical properties. For example, in some embodiments, the catheter comprises a polymeric material comprising a fluoropolymer comprising terminal polyfluoro-oligomeric groups, wherein the fluoropolymer is characterized by a polystyrene equivalent weight average molecular weight ($M_w$) greater than 13,000 Daltons (13 kDa). In particular embodiments, the fluoropolymer can contain less than 10% (w/w) (e.g., from 0% to 1.5%, 0% to 2%, 0.1% to 2.2%, 0.3% to 3%, 0% and 5%, or 0.5% to 5% (w/w)) trimer formed by reaction of one diisocyanate with two perfluorinated alcohols to form a low molecular weight fluoropolymer component containing no soft segment. In certain embodiments, the fluoropolymer can have a polystyrene equivalent weight average molar mass, $M_w$, of from 2,000 to 26,000 g/mole (e.g., 6,000±4,000, 8,000±4,000, 10,000±4,000, 12,000±4,000, 18,000±4,000, 20,000±4,000, 22,000±4,000, or 24,000±2,000 g/mole). In some embodiments, the fluoropolymer can have a polystyrene equivalent number average molar mass, $M_n$, of from 2,000 to 18,000 g/mole (e.g., 6,000±4,000, 8,000±4,000, 10,000±4,000, 13,000±2,000, 14,000±2,000, 15,000±2,000, or 16,000±2,000 g/mole). The fluoropolymer can have a polydispersity index of between 1.0 and 2.0 (e.g., a polydispersity of 1.1 to 1.4, 1.3 to 1.6, 1.35 to 1.55, 1.5 to 1.7, or 1.6 to 1.9). For example, the fluoropolymer can have a polystyrene equivalent weight average molar mass, $M_w$, of from 2,000 to 14,000 g/mole (e.g., 6,000±4,000, 8,000±4,000, or 12,000±2,000 g/mole), and/or a polystyrene equivalent number average molar mass, $M_n$, of from 2,000 to 12,000 g/mole (e.g., 6,000±4,000, 8,000±4,000, or 10,000±2,000 g/mole), and comprises between 0% and 3% (w/w) (e.g., from 0% to 1.5%, 0% to 2%, 0.1% to 2%, 0.1% to 2.2%, 0.3% to 2.2%, or 0.5% to 2.5% (w/w)) trimer. Alternatively, the fluoropolymer can have a polystyrene equivalent weight average molar mass, $M_w$, of from 14,000 to 26,000 g/mole (e.g., 18,000±4,000, 20,000±4,000, or 22,000±4,000 g/mole), and/or a polystyrene equivalent number average molar mass, $M_n$, of from 10,000 to 16,000 g/mole (e.g., 12,000±2,000 or 14,000±2,000 g/mole), and comprises between 0% and 3% (w/w) (e.g., from 0% to 1.5%, 0% to 2%, 0.1% to 2%, 0.1% to 2.2%, 0.3% to 2.2%, or 0.5% to 2.5% (w/w)) trimer. Fluoropolymer of desired size distribution and composition can be prepared, for example, by reducing the amount of diisocyanate used to make the fluoropolymer and/or by fractionating (i.e., by column chromatograph, dialysis, or extraction) the fluoropolymer.

In certain embodiments, the present invention comprises catheter materials comprising polyurethane and additives comprising a radiopaque material and a fluoropolymer comprising terminal polyfluoro-oligomeric groups. The amount of additives within the catheter material is up to about 44 weight percent (wt %), preferably up to about 40 wt %, more preferably up to about 35 wt %, and most preferably up to about 33 wt % of the catheter material. The amount of the fluoropolymer is preferably 1.5 wt %-2.5 wt % of the catheter material. The amount of radiopaque material, if used, is preferably 25 wt %-35 wt %, and more preferably up to 30 wt % of the catheter material, though amounts may vary depending on the material used. For instance, barium-based fillers can be used at concentrations of up to 40, while bismuth-based fillers are used at concentrations up to 30% and metallic fillers such as tungsten can be used at up to 80% concentrations. The amount of colorant, if used, is preferably 2 wt % of the catheter material, and more preferably up to about 0.2 wt % of the catheter material. The inventors have found that the 3 Fr, 4 Fr, 5 Fr, 6 Fr and 7 F catheters described herein, when manufactured within these compositional limitations, possess outstanding anti-thrombogenic properties and mechanical properties. For example, such catheters having wall thicknesses within the range of 0.005 to 0.050 inches effectively minimized thrombus formation in in vivo, blood-containing environments while remaining intact and structurally sound when tested to pressures up to 325 psi at maximum flow rates of 6 mL/sec using viscous fluid of 11.8 centipoise, which is the pressure rating for power injectable catheters as previously described.

In certain embodiments, the present invention comprises catheter materials comprising polyurethane and a fluoropolymer additive comprising polyfluoro-oligomeric groups, wherein the fluoropolymer is preferably characterized by a polystyrene equivalent weight average molecular weight ($M_w$) greater than 13,000 Daltons (13 kDa), more preferably 14-26 kDa. Moreover, the fluoropolymer additive is preferably characterized by a polydispersity index that is between 1.0 and 2.0, more preferably between 1.0 and 1.5. As used herein, "polydispersity index" is used synonymously with heterogeneity index and is calculated by the polystyrene equivalent weight average molecular weight ($M_w$) divided by the polystyrene equivalent number average molecular weight ($M_n$).

While aspects of the invention have been described with reference to example embodiments thereof, it will be understood by those skilled in the art that various changes in form and details may be made therein without departing from the scope of the invention.

What is claimed is:

1. A catheter comprising:
    an elongated tubular structure comprising:
        a polymeric material;
        an outer surface, a proximal end, a distal end, and a lumen, wherein said outer surface and said lumen extend between said proximal and distal ends; and
        a wall thickness between said outer surface and said lumen, said wall thickness being at least 0.005 inches;
    wherein said polymeric material comprises polyurethane and additives, said additives comprising a radiopaque material and a polymer comprising terminal polyfluoro-oligomeric groups; and
    wherein said polymeric material is comprised of a positive amount of up to about 44 weight percent of said additives.

2. The catheter of claim 1, wherein said additives further comprise a colorant, and said polymeric material comprises a positive amount of up to about 2.0 weight percent of said colorant.

3. The catheter of claim 1, wherein said polymeric material comprises about 25 weight percent to about 35 weight percent of said radiopaque material.

4. The catheter of claim 3, wherein said polymeric material comprises about 1.5 weight percent to about 2.5 weight percent of said polymer comprising terminal polyfluoro-oligomeric groups.

5. The catheter of claim 4, wherein said radiopaque material comprises barium sulfate.

6. The catheter of claim 5, wherein said polymeric material comprises a positive amount of up to about 30 weight percent of said barium sulfate.

7. The catheter of claim 6, wherein said additives further comprise a colorant, and said polymeric material comprises a positive amount of up to about 0.2 weight percent of said colorant.

8. The catheter of claim 1, wherein said polymeric material is comprised of a positive amount of up to about 40 weight percent of said additives.

9. The catheter of claim 1, wherein said polymeric material is comprised of a positive amount of up to about 33 weight percent of said additives.

10. The catheter of claim 1, wherein said elongated tubular structure comprises a plurality of lumens.

* * * * *